(12) United States Patent
Greenough et al.

(10) Patent No.: US 7,971,485 B2
(45) Date of Patent: Jul. 5, 2011

(54) METHOD OF AND APPARATUS FOR TESTING WOODEN POLES

(75) Inventors: Rodney David Greenough, Brigg (GB); John Anthony Moran, Brigg (GB)

(73) Assignee: CPI Quetra Limited, Barnsley (GB)

( * ) Notice: Subject to any disclaimer, the term of this patent is extended or adjusted under 35 U.S.C. 154(b) by 231 days.

(21) Appl. No.: 12/309,826

(22) PCT Filed: Jul. 30, 2007

(86) PCT No.: PCT/GB2007/050458
§ 371 (c)(1), (2), (4) Date: Feb. 17, 2009

(87) PCT Pub. No.: WO2008/015477
PCT Pub. Date: Feb. 7, 2008

(65) Prior Publication Data
US 2009/0188320 A1     Jul. 30, 2009

(30) Foreign Application Priority Data

Jul. 31, 2006   (GB) ................................. 0615151.8

(51) Int. Cl.
   *G01N 29/12*   (2006.01)
(52) U.S. Cl. ............................. 73/602; 73/648; 702/39
(58) Field of Classification Search .................... 73/602, 73/645–648; 702/38, 39, 40
   See application file for complete search history.

(56) References Cited

U.S. PATENT DOCUMENTS

| 4,059,988 | A | | 11/1977 | Shaw | |
| 4,301,684 | A | * | 11/1981 | Thompson et al. | 73/602 |
| 4,399,701 | A | | 8/1983 | Dunlop | |
| 5,760,308 | A | * | 6/1998 | Beall et al. | 73/644 |
| 5,804,728 | A | * | 9/1998 | Beall et al. | 73/598 |
| 6,276,209 | B1 | * | 8/2001 | Schafer et al. | 73/597 |
| 6,367,330 | B1 | * | 4/2002 | Schafer | 73/598 |
| 2004/0069064 | A1 | * | 4/2004 | Blodgett | 73/579 |
| 2005/0011263 | A1 | * | 1/2005 | Harris | 73/579 |

FOREIGN PATENT DOCUMENTS

WO   WO 02/08749 A   1/2002

* cited by examiner

*Primary Examiner* — Hezron Williams
*Assistant Examiner* — Rose M Miller
(74) *Attorney, Agent, or Firm* — Jackson Walker, LLP

(57) ABSTRACT

A method of testing an elongate wooden element includes injecting an input acoustic signal into the element, detecting a return acoustic signal at a surface of the element, and determining a spectral profile for the return signal. In at least a predetermined range in the spectral profile, each resonance peak is detected whose amplitude exceeds a first predetermined value, and from the resonance peaks so detected the number of higher peaks is determined whose amplitude exceeds 3 dB. For each of said higher peaks a quality factor Q is calculated, a mean quality value $Q_m$ is determined, and $Q_m$ is then compared with a predetermined value to provide an indication of the presence or absence of external decay of the element. A ratio R of the number of higher peaks to the number of resonance peaks detected, and the statistical spread S of the average Q for the spectral profile, are calculated and compared with a predetermined boundary function $F_n(R,S)$ to determine acceptability or unacceptability of the pole.

14 Claims, 6 Drawing Sheets

METHOD OF AND APPARATUS FOR TESTING WOODEN POLES

FIELD OF THE INVENTION

This invention relates to a method of and an apparatus for testing wooden poles and other wooden structural elements, for example to detect degradation due to rot.

BACKGROUND TO THE INVENTION

While the invention relates to the testing of wooden structural elements in general, one common example of a structural element that needs monitoring is the utility pole. Utility poles are typically a length of the trunk of a pine tree. After cutting, the poles are seasoned for sufficient time to dry and stabilise the timber, and are then treated with preservative chemicals. The poles are intended to have a pre-determined length buried in the ground, to provide sufficient structural stability. In some conditions, such poles can remain serviceable for many years—some have remained sound for several decades.

In some conditions, and/or where treatment of the timber has been insufficient after cutting, rot can occur, substantially reducing the safe working life of the pole. When work is to be done on cables supported by the pole, for example, it is typically acceptable for a ladder to be leant against the pole to support the person doing the work. Before work commences, it is necessary to test the state of the pole to ensure that it has sufficient strength. The simplest form of testing has been carried out by striking the pole with a hammer and listening to the resultant sound. With careful training, a person can distinguish by listening to this resultant sound between a sound pole and one which has been weakened by decay. If the pole is deemed unsafe for ladder access, the work may need to be carried out from an access hoist, which involves extra cost and possible delay, but it may become necessary for the pole to be replaced, which is even more costly. It is therefore important to ensure that testing is as accurate as possible, and accuracy is difficult to achieve where the test criteria are subjective.

There have been proposals for mechanically inducing acoustic energy into the pole, recording the output from an audio transducer attached to the pole, and analysing the output to provide an indication of the state of the timber. Earlier techniques simulated the manual testing technique, with a high energy blow to the pole serving to cause the pole to "ring" at the resonant frequencies thereof, with the transducer then picking up the response. This is imprecise, because a wide band of acoustic frequencies is generated simultaneously with little or no control of the spectral profile of the input acoustic energy, so initiating resonances due the excitement of other waveforms. Furthermore, the high-energy pulses required, typically delivered manually, to generate sufficient acoustic power cause local damage to the structure. In some instances, the results obtained were no more accurate than could be obtained by a trained person listening to the sound.

U.S. Pat. No. 4,399,701 discloses a system involving the generation of a continuous longitudinal acoustic wave by inserting transducers (for example piezoelectric transducers) into slots cut into the pole at locations spaced apart along is its length. The input acoustic frequency is varied over a range that includes, say the first twenty standing wave harmonic frequencies of the pole. If the output contains harmonic resonances, then this can be taken as an indication of a sound pole, while a pole containing rot is said to yield resonant frequencies which are not in harmonic relationship with one another. It is not explained how the judgment on these issues is made.

A major disadvantage of this technique is that it necessitates the cutting of slots into the pole, something that utilities operators would consider highly undesirable, since it would tend to weaken the pole and to provide a possible future route into the interior of the pole of damaging moisture and attacking organisms. It is therefore desirable to provide a testing method which is non-invasive and which provides a more accurate indication of the state of the wood in the pole.

SUMMARY OF THE INVENTION

According to the invention, there is provided a method of testing an elongate wooden element, comprising injecting an input acoustic signal into the element, detecting a return acoustic signal at a surface of the element, determining a spectral profile for the return signal, detecting in at least a predetermined range in the spectral profile each resonance peak whose amplitude exceeds a first predetermined value, determining from the resonance peaks so detected the number of higher peaks whose amplitude exceeds 3 dB, calculating for each of said higher peaks a quality factor Q, determining a mean quality value $Q_m$, and comparing $Q_m$ with a predetermined value to provide an indication of the presence or absence of external decay of the element, calculating a ratio R of the number of higher peaks to the number of resonance peaks detected, calculating the statistical spread S of the average Q for the spectral profile, and comparing the values of R and S with a predetermined boundary function $F_n(R,S)$ to determine acceptability or unacceptability of the pole.

The boundary is preferably defined by $x = a \cos^{2/r} t$ $y = b \sin^{2/r} t$ where the constants a represents the value of S in the limit of R=100% and the constant b represents the value of R in the limit of S=0%, r is a constant that regulates the curvature of the boundary.

The critical values for a, b and r are suitably assigned on the basis of multiple observations on poles (for example) known to have no decay and poles known to have internal and/or external decay.

The wooden element may be a utility pole, and the pole may have one end portion thereof buried in the ground in conventional manner. However, the method of the invention may also be applicable to other wooden elements, such as structural timbers in situ, for example piles, rafters and joists or timber frame elements.

The invention also provides apparatus for testing an elongate wooden element, comprising an acoustic transmit transducer attachable temporarily and non-invasively to an external side surface of the element, a signal generator for applying an acoustic signal to the acoustic signal to the transmit transducer at an amplitude sufficient to couple acoustic energy into the element, a controller connected to the signal generator for controlling the frequency of the acoustic signal, and a receive transducer attachable to an external surface of the element and connected to the controller, the controller being programmed to:

detect in at least a predetermined range in the spectral profile each resonance peak whose amplitude exceeds a first predetermined value;

determine from the resonance peaks so detected the number of higher peaks whose amplitude exceeds 3 dB;

calculate for each of said higher peaks a quality factor Q, determine a mean quality value $Q_m$, and compare $Q_m$ with a predetermined value to provide an indication of the presence or absence of external decay of the element;

calculate a ratio R of the number of higher peaks to the number of resonance peaks detected;

calculate the statistical spread S of the average Q for the spectral profile; and compare the values of R and S with a predetermined boundary function $F_n(R,S)$ to determine acceptability or unacceptability of the pole.

The transmit transducer may be a magnetostrictive transducer, since this type of transducer is capable of generating a high power and is of low compliance. The receive transducer may for example be an accelerometer, but may also be a magnetostrictive transducer. In one embodiment of the invention, the transmit and receive transducers are the same single transducer.

The high power sound waves generated by the transducer can couple sufficient of the transversely-applied energy into all modes to resonate the structure. This is due to diffraction and/or mode-coupling. Diffraction occurs due to the finite size of the radiating face of the transducer, and mode conversion works due to the anisotropy of sound speed in wood.

This technique is also aided by the high impedance mismatch between the wood and air, between wood and the ground, in the case of a pole having an end buried in the ground, and by the aspect ratio of the poles (for utility poles the typical ratio of length to diameter is about 30:1). Typically these lead to relatively large Q values for good quality poles (e.g. 30), thereby enabling the detection of pole decay when the ideal conditions for the excitement of transverse waves, and the establishment of transverse mode standing waves, deteriorate. (Q is the quality factor, conventionally defined as $$Q = \frac{f_0}{\Delta f},$$

where $f_0$ is the resonant frequency and $\Delta f$ is the bandwidth at −3 dB from the peak.)

The technique is especially effective below ground, effectively measuring the increased loss of energy from (a) a decay pocket leaking energy into the ground due to the reduced acoustic impedance mismatch between the pole and the ground (if the impedances of the decayed wood and the ground were the same, all the sound would escape and there would be no resonance) and/or (b) the soft spongy nature of the decayed wood increasing inherent acoustic absorption.

The method of the invention is totally non-destructive—the transmit transducer is temporarily attached to the side of the wooden element (e.g. the pole), for example by a strap passing around the pole, and does not require the formation of any apertures in the wood which might lead to the entry of decay organisms or wood-attacking insects.

It is possible by the method and apparatus of the invention to determine whether the length of a wooden element, for example a utility pole, differs from the specified length. Since the length of a utility pole is known prior to installation, it can be used to determine the predicted resonant frequencies of the element that subsequent measurements can confirm. It will be appreciated that the pole length can only be gauged with certainty if the longitudinal velocity of sound in the pole is known. Then the frequencies of the transverse mode resonances can be predicted, and the observed frequencies compared with them.

The controller may be linked to or include storage means to store data relating to each test, for example to be downloaded subsequently to a central data base. This local data may be stored in internal non-volatile memory and/or on a removable memory card. This will allow central collection of data and preventative maintenance programmes to be developed as the database grows.

The apparatus may incorporate a Global Positioning System (GPS) receiver to enable the time and position of the tests to be accurately recorded. In the case of utility poles, since they are rarely closer together than the 1 meter resolution typically achievable, this will eliminate the need to identify the pole number.

In the case of multimode excitation it would be possible to segregate the modes of different sound waves propagated (e.g. longitudinal or transverse waves) to enable observation of their individual spectra and permit measurements of their corresponding standing wavelengths, velocities and acoustic damping.

While the positions of the transmit and receive transducers on the wooden element affect the observed spectrum, the exact positioning is not critical; corresponding variations in the observed spectrum can be accounted for and analysed accordingly.

BRIEF DESCRIPTION OF THE DRAWINGS

In the drawings, which illustrate exemplary embodiments of the invention.

DETAILED DESCRIPTION OF THE ILLUSTRATED EMBODIMENTS

Figure 1:
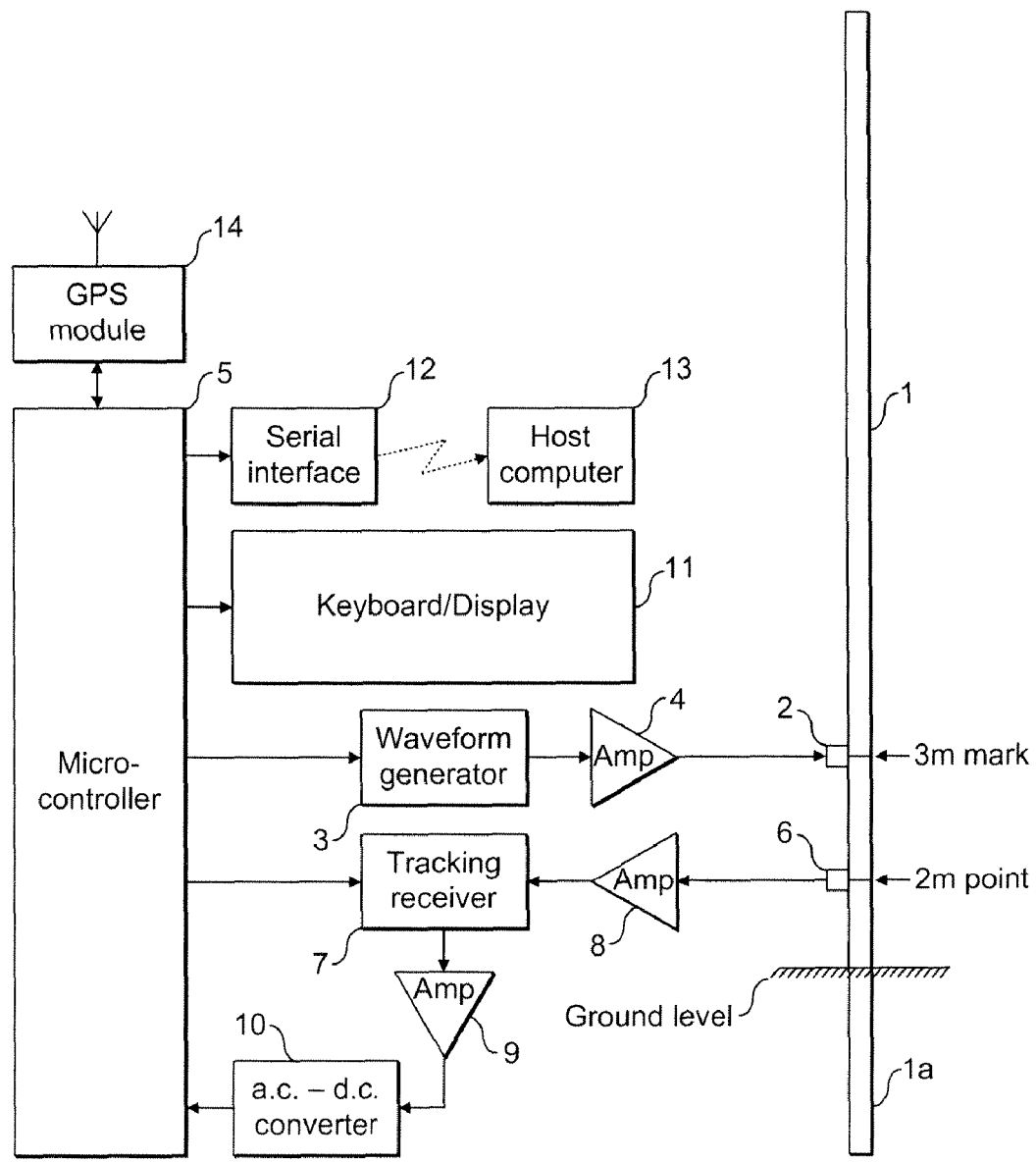
FIG. 1 is a diagrammatic representation of apparatus with separate transmit and receive transducers.

Referring first to FIG. 1, a utility pole 1 has one end thereof 1a buried in the ground. If decay occurs in the buried end 1a, the pole may become inadequately supported and could fail when abnormally loaded, for example by a maintenance engineer climbing a ladder placed against it. The test apparatus consists of a transmit transducer 2 in the form of a magnetostrictive actuator which is temporarily clamped against the surface of the pole, for example at the 3 meter mark relative to the lowermost end, by means of a removable strap, for example. The driving signal for the transducer 2 is supplied by a waveform generator 3 by way of an amplifier 4. The waveform generator is controlled by a microcontroller 5.

A receive transducer 6, for example an accelerometer, is similarly temporarily clamped to the external surface of the pole 1 at a distance from the transmit transducer 2. For example, it can be mounted at the 2 meter position from the end of the pole. The output from the transducer 6 passes to a tracking receiver 7 by way of an amplifier 8. The tracking receiver 7 is also controlled by the microcontroller 5. The signal received by the tracking receiver passes through an amplifier 9 and an analogue to digital converter 10 whose output is connected to the microcontroller 5. A keyboard and display 11 are connected to the microcontroller to enable the operator to control the apparatus. The serial or other interface 12 is provided for communication between the microcontroller and a host computer 13 to permit downloading of data to the host computer. A GPS module 14 provides accurate time and position data to the microcontroller 5.

The microcontroller is programmed to sweep the frequency of the audio signal applied to the transmit transducer 2 in 1000 steps on a logarithmic scale across a frequency decade which encompasses the fundamental resonant frequency of the element and/or at least one harmonic thereof, typically from about 100 Hz to about 1000 Hz. The signal received by the receive transducer 6 is sampled by the converter 10 for each step, and the resultant frequency and voltage samples are processed by the microprocessor to detect the number N of all discernable peaks in the spectral range arising from the acoustic response of the pole. It might be appropriate to define this as encompassing all peaks having an amplitude greater than a predetermined value, which might be set at 0.5 dB or 1 dB, for example. The microprocessor then detects a number n of higher peaks out of this total having an amplitude greater than 3 dB. For each of the peaks whose amplitude exceeds 3 dB a quality factor Q is calculated in accordance with well-known procedures. An average Q, $Q_m$, is then calculated for a predetermined spectral range, typically 200 Hz to 1000 Hz. The microprocessor compares this with a predetermined value to give an indication that external decay is present when $Q_m$ is less than the predetermined value. In the assessment of pine poles carrying communications wires, for example, a $Q_m$ figure below 14 has been found to be indicative of the presence of external decay.

Next, the microprocessor calculates the ratio R of the number of higher peaks n to the total number of peaks N. This factor (a) gauges the number of significant resonance peaks in the spectral range and distinguishes these from smaller spurious peaks attributable, for example, to noise, and (b) assesses the break-up of a spectrum that is identified with the occurrence of internal decay.

Using the Q values calculated for the spectral range, the microprocessor is programmed to calculate the standard deviation about the mean $Q_m$. This is also a factor that enables the detection, and gauges the extent, of internal decay in the wood.

Figure 3:
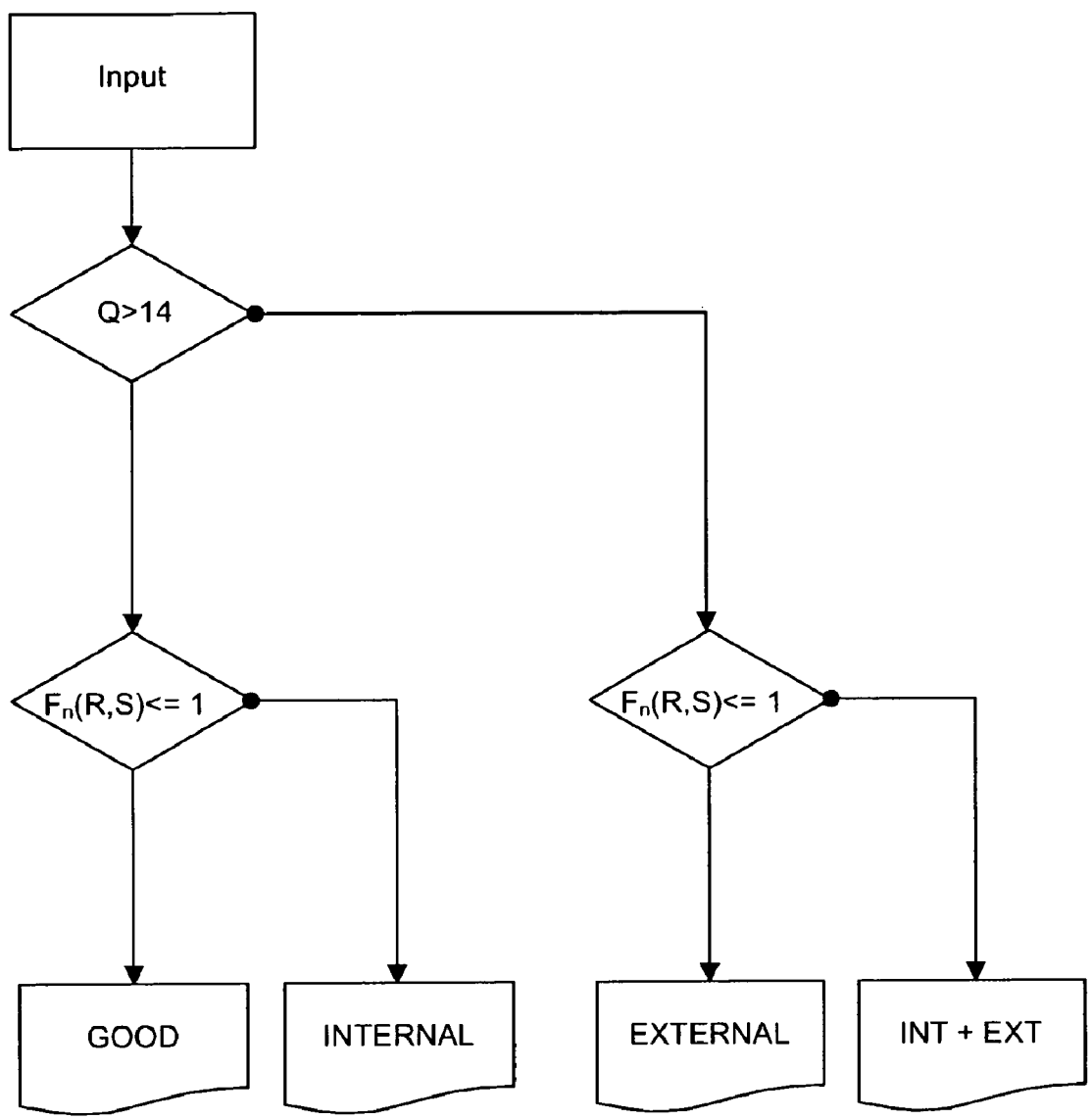
FIG. 3 illustrates an algorithm by which the determination of the nature of the wooden element may be carried out.

Typical critical values for each parameter that are employed in the sort process are shown in the flow diagram illustrated in FIG. 3. Although $Q_m$ is a single valued independent parameter, R and S are not. Their interdependence is expressed as a function $F_n(R,S)$, chosen to generate multiple pairs of values (R, S) that enable the discrimination between spectra characteristic of 'good' poles and those containing decay.

Figure 2:
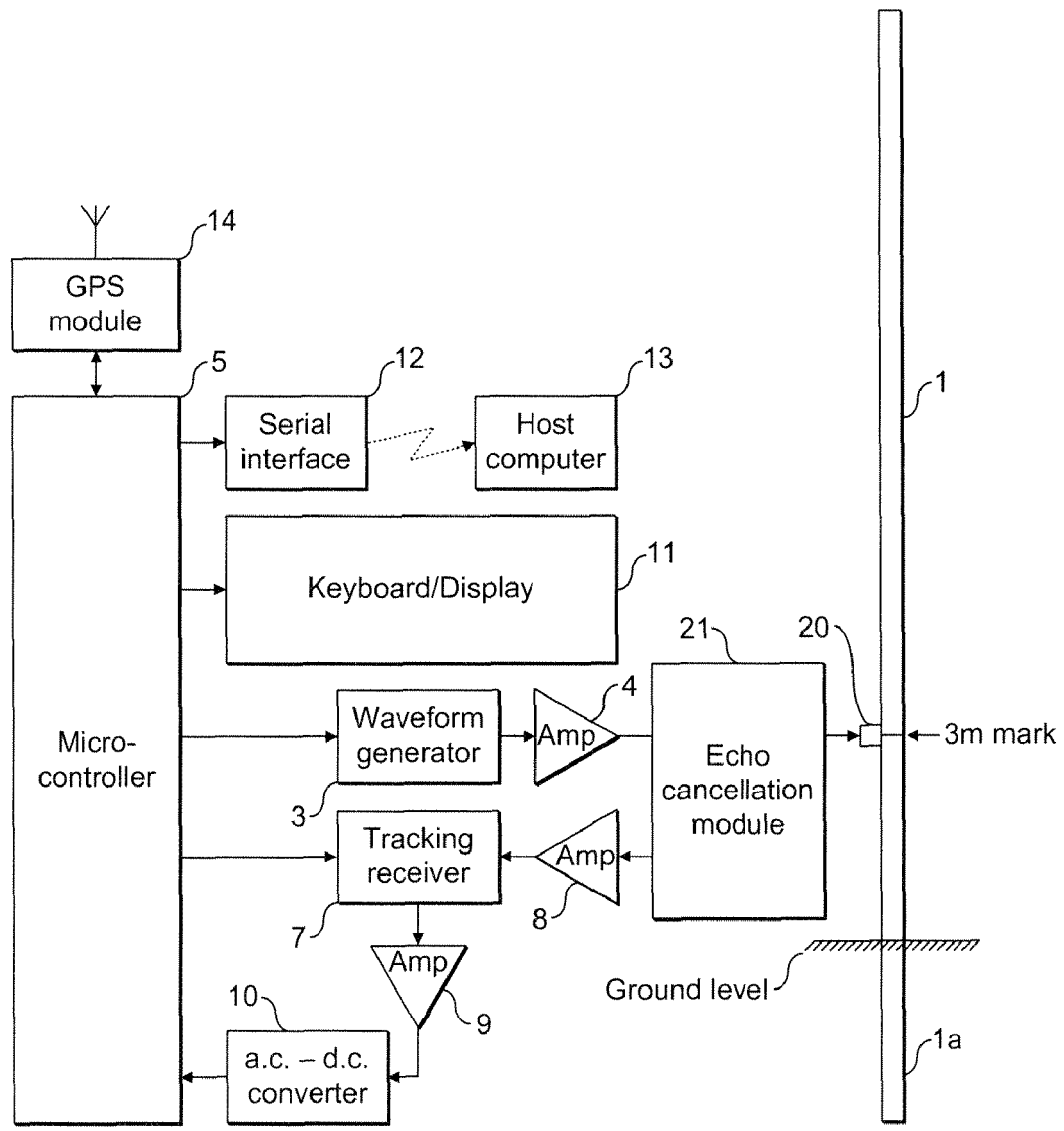
FIG. 2 is a diagrammatic representation of corresponding apparatus with a combined transmit and receive transducer.

Referring now to FIG. 2, in an alternative configuration, a single transmit/receive magnetostrictive transducer 20 is used, temporarily clamped to the post at the 3 meter mark. An echo cancellation module 21 is connected between the transducer 20 and the input and output amplifiers 4 and 8. It will be recognised by those skilled in the art that fast digital signal processors can be programmed to perform echo cancellation. The remainder of the apparatus is as described with reference to FIG. 1, and the same reference numerals are used in the Figure.

Figure 4:
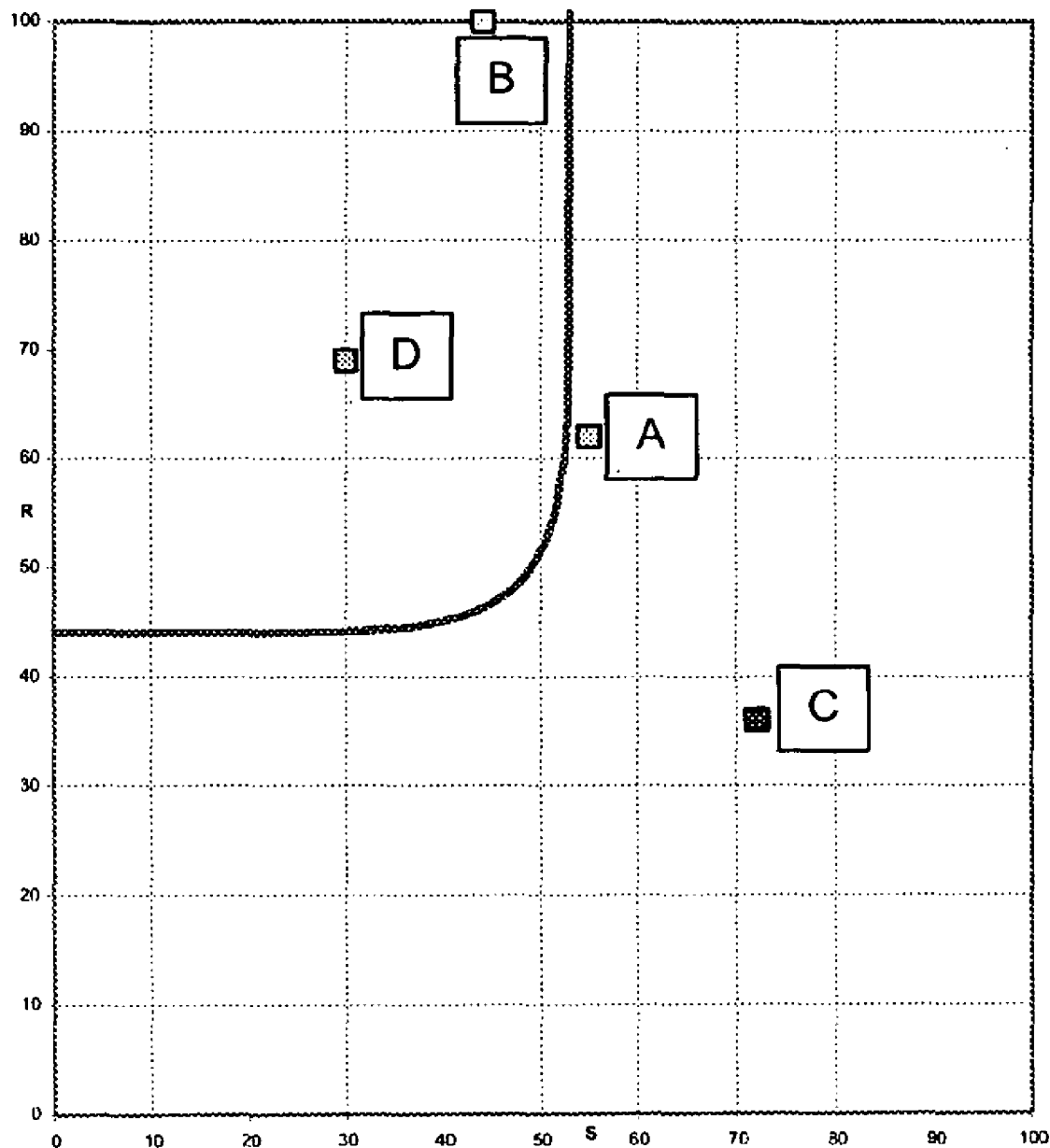
FIG. 4 is a graph plotting R against S values and illustrating differentiation between acceptable and unacceptable wooden communications poles tested by the apparatus of the invention.

FIG. 4 illustrates a plot of R against S values for four different test poles A, B, C and D. A boundary function is illustrated by the line F in the graph. By comparing the relationship between each plot and the boundary function, an assessment of the state of the pole can be made. The locus of points defining the boundary between acceptable and unacceptable poles has been defined on the basis of the two interdependent parameters R & S. In parametric form the equation of the boundary is given by $$x = a \cos^{2/r} t$$

$$y = b \sin^{2/r} t$$

where the constants a represents the value of S in the limit of R=100% and the constant b represents the value of R in the limit of S=0%, r is a constant that regulates the curvature of the boundary. The critical values for a, b and r are assigned on the basis of multiple observations on poles (for example) known to have no decay and poles known to have internal and/or external decay.

A number of poles have been tested using the apparatus and method described, and samples of the poles have then been examined to determine the boundary function. The four test poles A, B, C and D illustrate respectively a pole with both internal and external decay, a pole with external decay only, a pole with internal decay only, and a sound pole without significant decay. It will be seen from FIG. 4 that poles B and D fall within the boundary demarcating acceptable poles, while A and C fall outside and are therefore deemed unacceptable. For example, they might be scheduled for replacement, and until replacement a ban might be imposed on climbing the poles or placing ladders against them.

Figure 5:
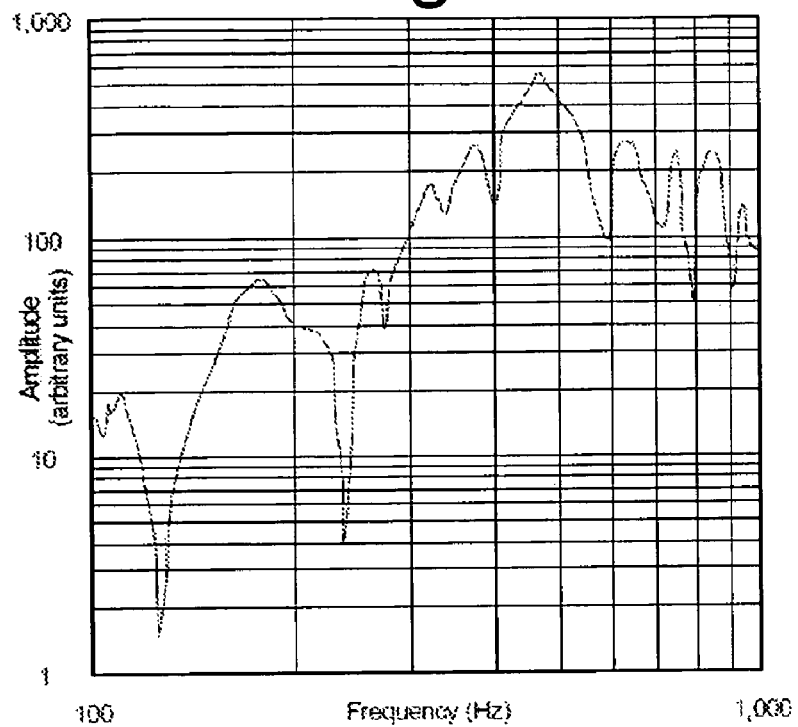
FIG. 5 is a plot of voltage against frequency for pole A in FIG. 4, exhibiting both internal and external decay, and therefore unacceptable.

FIGS. 5 to 8 are graphs illustrating the frequency spectrum obtained for each of poles A, B, C and D. FIG. 5 illustrates the spectrum for a pole having both internal and external decay. It will be seen that the peaks are generally broad, leading to a lower Q factor, indicating external decay, but with approximately half the peaks exceeding 3 dB, leading to a reasonable R value. The statistical spread of peaks S is, however, higher than for the acceptable level, placing the test outside the acceptable region, and indicating the presence of internal decay as well as external decay.

Figure 6:
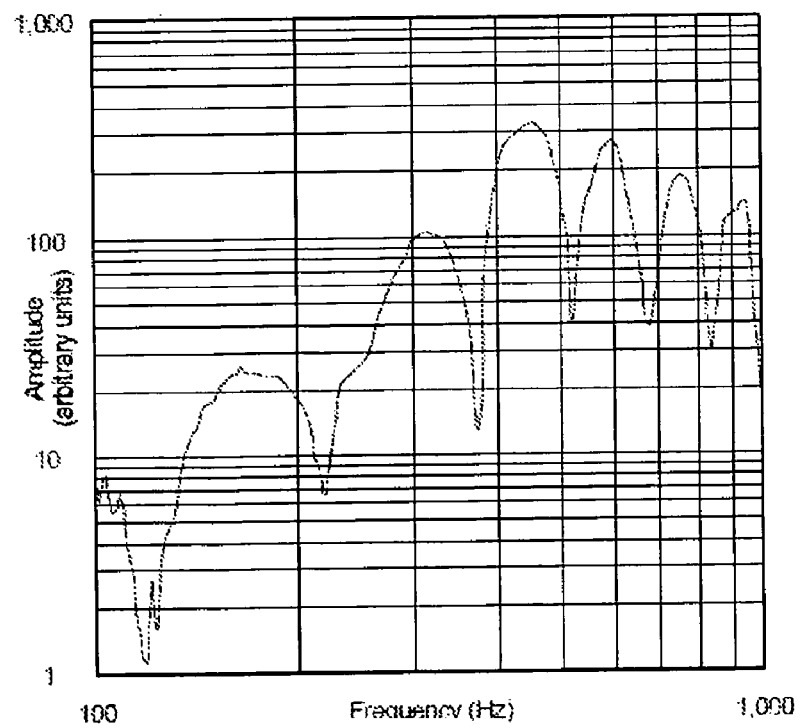
FIG. 6 is a corresponding plot for pole B in FIG. 4, exhibiting a degree of external decay only, and therefore unacceptable.

FIG. 6 exhibits distinct, but broad peaks, yielding a $Q_m$ of about 7, which indicates the presence of external decay. The high proportion of peaks above 3 dB gives a high R value. The statistical spread S is 44%. These indicate the absence of internal decay and place the pole within the region of acceptability for internal decay, but the external decay indicated by the low Q value renders this pole unacceptable.

Figure 7:
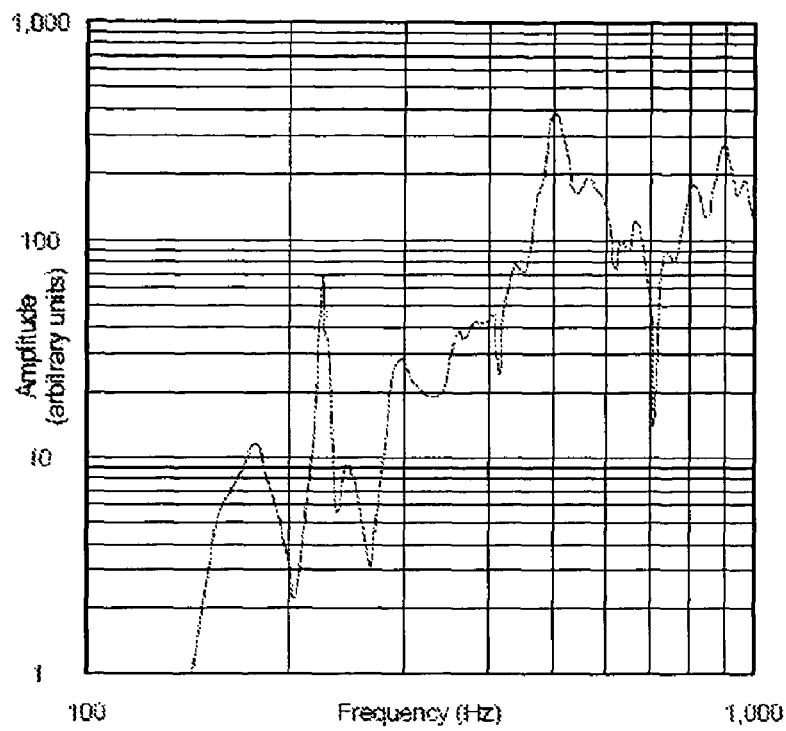
FIG. 7 is a corresponding plot for pole C in FIG. 4, exhibiting internal decay, and therefore unacceptable.

FIG. 7 has a number of good distinct peaks yielding a $Q_m$ of about 19, which indicates an absence of external decay. However, there are many lower peaks, yielding a low R value. The statistical spread S is also low, these factors together indicating the presence of internal decay and placing the pole in the unacceptable region.

Figure 8:
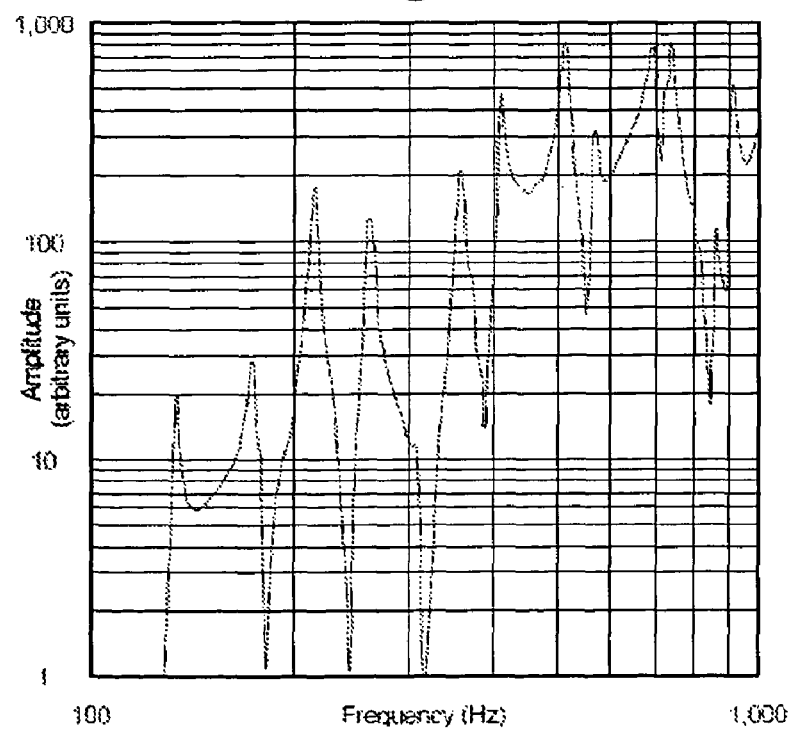
FIG. 8 is a corresponding plot for pole D in FIG. 4, exhibiting no decay and therefore classed as acceptable.

FIG. 8 illustrates the spectrum of a sound pole. The spectrum shows a good number of sharp resonance peaks, yielding a $Q_m$ of about 18, and R value of 69 and an S value of 30, placing the pole firmly in the acceptable region.

The invention claimed is:

1. A method of testing an elongate wooden element, comprising injecting an input acoustic signal into the element, detecting a return acoustic signal at a surface of the element, determining a spectral profile for the return signal, detecting in at least a predetermined range in the spectral profile each resonance peak whose amplitude exceeds a first predetermined value, counting the number of said detected resonance peaks, determining from the resonance peaks so detected the number of higher peaks whose amplitude exceeds 3 dB, calculating for each of said higher peaks a quality factor Q, determining a mean quality value $Q_m$, and comparing $Q_m$ with a predetermined value to provide an indication of the presence or absence of external decay of the element, calculating a ratio R of the number of higher peaks to the number of resonance peaks detected, calculating the statistical spread S of the mean quality value $Q_m$ for the spectral profile, and comparing the values of R and S with a predetermined boundary function $F_n(R,S)$ to determine acceptability or unacceptability of the elongate wooden element.

2. A method according to claim 1, wherein the boundary function is given by $$x = a \cos^{2/r} t$$

$$y = b \sin^{2/r} t$$

where the constants a represents the value of S in the limit of R=100% and the constant b represents the value of R in the limit of S=0%, r is a constant that regulates the curvature of the boundary.

3. A method according to claim 1, comprising injecting the input acoustic signal into the element using a magnetostrictive transducer.

4. A method according to claim 1, comprising detecting the return acoustic signal using a magnetostrictive transducer.

5. A method according to claim 1, comprising varying the frequency of the input acoustic signal during injection thereof.

6. A method according to claim 5, wherein the frequency is swept across a predetermined range of frequencies.

7. A method according to claim 6, wherein the range is 100 Hz to 1000 Hz.

8. Apparatus for testing an elongate wooden element, comprising an acoustic transmit transducer attachable temporarily and non-invasively to an external side surface of the element, a signal generator for applying an acoustic signal to the transmit transducer at an amplitude sufficient to couple acoustic energy into the element, a controller connected to the signal generator for controlling the frequency of the acoustic signal, and a receive transducer attachable to an external surface of the element and connected to the controller, the controller being programmed to:

detect in at least a predetermined range in the spectral profile each resonance peak whose amplitude exceeds a first predetermined value;

count the number of said detected resonance peaks;

determine from the resonance peaks so detected the number of higher peaks whose amplitude exceeds 3 dB;

calculate for each of said higher peaks a quality factor Q, determine a mean quality value $Q_m$, and compare $Q_m$ with a predetermined value to provide an indication of the presence or absence of external decay of the element;

calculate a ratio R of the number of higher peaks to the number of resonance peaks detected;

calculate the statistical spread S of the mean quality value $Q_m$ for the spectral profile; and compare the values of R and S with a predetermined boundary function $F_n(R,S)$ to determine acceptability or unacceptability of the elongate wooden element.

9. Apparatus according to claim 8, wherein the transmit transducer is a magnetostrictive transducer.

10. Apparatus according to claim 8, wherein the receive transducer is a magnetostrictive transducer.

11. Apparatus according to claim 8, wherein the transmit transducer is adapted to operate additionally as the receive transducer.

12. Apparatus according to claim 8, wherein the controller is programmed to vary the frequency of the signal applied to the transmit transducer within a range of frequencies.

13. Apparatus according to claim 12, wherein the controller frequency is swept over said range of frequencies.

14. Apparatus according to claim 13, wherein the range is 100 Hz to 1000 Hz.

* * * * *